(12) United States Patent
Mizutani et al.

(10) Patent No.: US 10,518,026 B2
(45) Date of Patent: Dec. 31, 2019

(54) DRUG ADMINISTRATION MECHANISM, METHOD FOR USING DRUG ADMINISTRATION MECHANISM, AND PUMP UNIT FOR DRUG ADMINISTRATION MECHANISM

(71) Applicant: NITTO DENKO CORPORATION, Osaka (JP)

(72) Inventors: Toru Mizutani, Osaka (JP); Takashi Tsuji, Osaka (JP); Hiroyuki Shinohara, Osaka (JP)

(73) Assignee: NITTO DENKO CORPORATION, Ibaraki-shi, Osaka (JP)

(*) Notice: Subject to any disclaimer, the term of this patent is extended or adjusted under 35 U.S.C. 154(b) by 62 days.

(21) Appl. No.: 15/531,208

(22) PCT Filed: Nov. 26, 2015

(86) PCT No.: PCT/JP2015/083297
§ 371 (c)(1),
(2) Date: May 26, 2017

(87) PCT Pub. No.: WO2016/084919
PCT Pub. Date: Jun. 2, 2016

(65) Prior Publication Data
US 2017/0326291 A1 Nov. 16, 2017

(30) Foreign Application Priority Data

Nov. 27, 2014 (JP) .................................. 2014-240045

(51) Int. Cl.
*A61M 37/00* (2006.01)
*A61M 5/142* (2006.01)
(Continued)

(52) U.S. Cl.
CPC ............ *A61M 5/142* (2013.01); *A61M 5/145* (2013.01); *A61M 5/16854* (2013.01);
(Continued)

(58) Field of Classification Search
CPC ...... A61M 5/16854; A61M 2205/0244; A61M 2205/3334; A61M 2205/8206;
(Continued)

(56) References Cited

U.S. PATENT DOCUMENTS 3,242,920 A    3/1966  Andersen
4,303,376 A *  12/1981 Siekmann ......... A61M 5/14224
                                                 417/360
(Continued)

FOREIGN PATENT DOCUMENTS

CN    201279316 Y    7/2009
EP    2 327 430 A1   6/2011
(Continued)

OTHER PUBLICATIONS

International Search Report dated Feb. 23, 2016 issued by the International Searching Authority in counterpart International Application No. PCT/JP2015/083297 (PCT/ISA/210).
(Continued)

*Primary Examiner* — Rebecca E Eisenberg
(74) *Attorney, Agent, or Firm* — Sughrue Mion, PLLC

(57) ABSTRACT

The present invention relates to a dosing mechanism including: a body; and a pump unit (3) that is attached to the body, in which the pump unit (3) includes: a pump (31) in which a volume of a solution feeding part therein repeats expansion and shrinkage, thereby sucking a medicine from a medicine vessel and discharging the medicine to a patient; a suction-side pipe (333) that extends from the pump (31) toward the medicine vessel; a discharge-side pipe (343) that extends from the pump (31) toward the patient; a relief pipe (35, 35a)

(Continued)

whose one end (351) is connected to the discharge-side pipe (343) while the other end (352) is located in a part whose pressure is lower than pressure inside the discharge-side pipe when the medicine is dosed; and a relief pipe on-off valve (36, 36*a*) that opens and closes the relief pipe (35, 35*a*), a use method of a dosing mechanism, and a pump unit for a dosing mechanism.

9 Claims, 6 Drawing Sheets

(51) Int. Cl.
  *A61M 5/145* (2006.01)
  *A61M 5/168* (2006.01)
  *A61M 39/22* (2006.01)
  *F04B 7/00* (2006.01)
  *F04B 43/00* (2006.01)

(52) U.S. Cl.
  CPC ........... *A61M 39/22* (2013.01); *F04B 7/0042* (2013.01); *F04B 43/0081* (2013.01)

(58) Field of Classification Search
  CPC .. A61M 5/142; A61M 5/168; A61M 5/16881; A61M 5/365; A61M 2005/14268; A61M 2205/3351; A61M 2205/3355
  See application file for complete search history.

(56) References Cited

U.S. PATENT DOCUMENTS

| | | |
|---|---|---|
| 5,098,384 A | 3/1992 | Abrams |
| 6,905,479 B1 | 6/2005 | Bouchard et al. |
| 8,728,020 B2 | 5/2014 | Caleffi et al. |
| 9,119,915 B2 | 9/2015 | Kawamura |
| 2010/0280430 A1 | 11/2010 | Caleffi et al. |
| 2012/0265125 A1 | 10/2012 | Kawamura |
| 2015/0367068 A1 | 12/2015 | Kawamura |

FOREIGN PATENT DOCUMENTS

| | | |
|---|---|---|
| JP | 56-11064 A | 2/1981 |
| JP | 2011-177411 A | 9/2011 |
| JP | 2013-117211 A | 6/2013 |
| WO | 2009/044221 A1 | 4/2009 |

OTHER PUBLICATIONS

Written Opinion dated Feb. 23, 2016 issued by the International Searching Authority in counterpart International Patent Application No. PCT/JP2015/083297 (PCT/ISA/237).
Extended European Search Report dated Aug. 24, 2018, issued by the European Patent Office in counterpart European Application No. 15863031.9.
Notification of Reasons for Refusal dated Jun. 8, 2018, issued by the Japanese Patent Office in counterpart Japanese Application No. 2014-240045.
Office Action dated Oct. 5, 2018 by the Japanese Patent Office in counterpart Japanese Patent Application No. 2014-240045.
Communication dated Jun. 4, 2019 issued by the State Intellectual Property Office of P.R. China in counterpart Chinese Application No. 201580064192.5.
Communication dated Feb. 15, 2019, issued by the Taiwanese Patent Office in counterpart Taiwan Application No. 104139751.

* cited by examiner

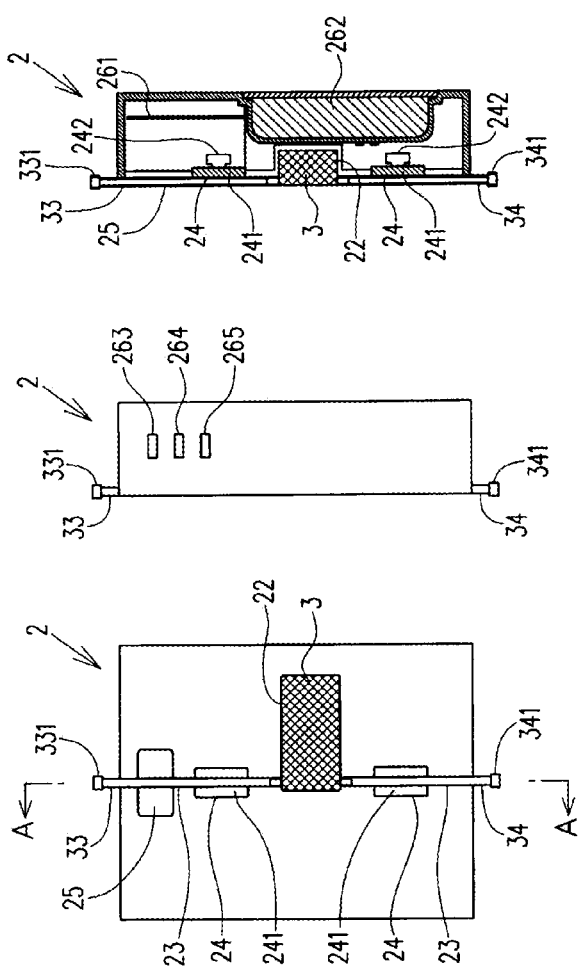

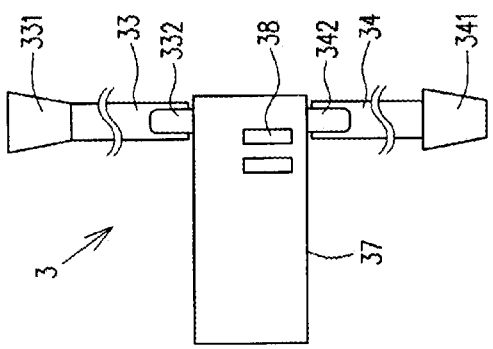
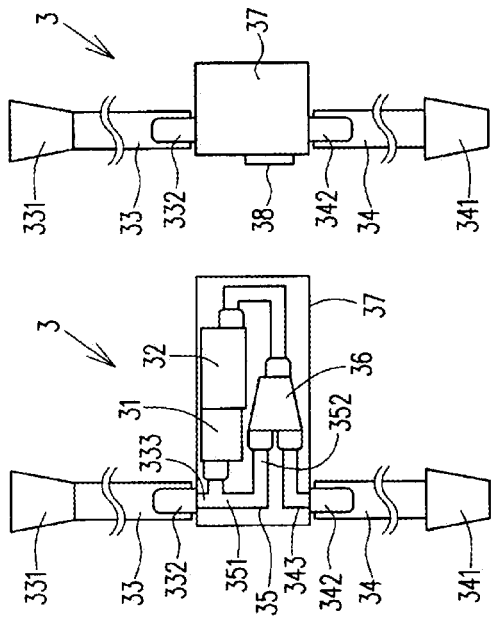
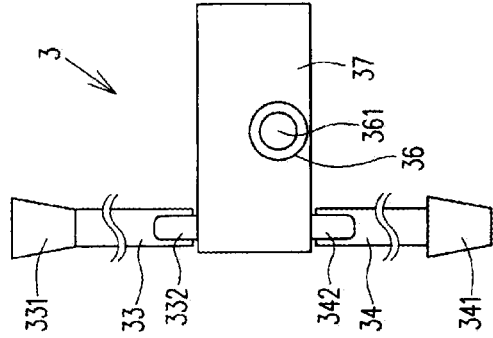

DRUG ADMINISTRATION MECHANISM, METHOD FOR USING DRUG ADMINISTRATION MECHANISM, AND PUMP UNIT FOR DRUG ADMINISTRATION MECHANISM

TECHNICAL FIELD

The present invention relates to a dosing mechanism for dosing a patient with liquid medicine filled in a medicine vessel, a use method of a dosing mechanism, and a pump unit for a dosing mechanism.

BACKGROUND ART

For example, an infusion volume control apparatus is disclosed in Patent Document 1 as a dosing mechanism for dosing a patient with liquid medicine (medicinal solution) filled in a medicine vessel. The apparatus has a pump (micro-pump) for feeding the solution based on expansion and shrinkage of a pump chamber.

In a solution feeding system in which the apparatus disclosed in Patent Document 1 has been installed, a backward flow can be prevented due to the configuration of the pump even if a tube connected to the discharge side of the pump is closed. As a result, the pump may be driven continuously until a large amount of the medicinal solution stays in a section between the pump and the closed site.

However, even when the tube is closed, no countermeasure is taken on the apparatus side (although Patent Document 1 describes a control unit for detecting occurrence of an abnormal event, there is no suggestion about an event where the tube is closed). Therefore, when a medical worker such as a nurse releases the closed state, the patient may be dosed in a rush with the large amount of the medicinal solution which has stayed in the tube.

BACKGROUND ART DOCUMENT

Patent Document

Patent Document 1: JP-A-2011-177411

SUMMARY OF THE INVENTION

Problems that the Invention is to Solve

It is therefore an object of the present invention to provide a dosing mechanism capable of suppressing a patient from being dosed with a medicinal solution in a rush as soon as closed state is released even when the closing occurs in a pipe such as a tube, a use method of a dosing mechanism, and a pump unit for a dosing mechanism.

Means for Solving the Problems

The present invention relates to a dosing mechanism for dosing a patient with liquid medicine filled in a medicine vessel, including: a body; and a pump unit that is attached to the body, in which the pump unit includes: a pump in which a volume of a solution feeding part therein repeats expansion and shrinkage, thereby sucking the medicine from the medicine vessel and discharging the medicine to the patient; a suction-side pipe that extends from the pump toward the medicine vessel; a discharge-side pipe that extends from the pump toward the patient; a relief pipe whose one end is connected to the discharge-side pipe while the other end is located in a part whose pressure is lower than pressure inside the discharge-side pipe when the medicine is dosed; and a relief pipe on-off valve that opens and closes the relief pipe.

With this configuration, the relief pipe on-off valve is opened before release of the closed state, so that an excessive amount of the medicinal solution staying in a section between the pump and the closed site can be eliminated from a medicine channel. It is therefore possible to suppress the staying medicinal solution from flowing toward the patient due to the release of the closed state.

Additionally, the other end of the relief pipe may be connected to the suction-side pipe.

With this configuration, an excessive amount of the medicinal solution staying in the section between the pump and the closed site can be returned to the suction-side pipe. Thus, the excessive medicinal solution can be used effectively.

Additionally, the relief pipe on-off valve may be configured to be opened manually.

With this configuration, a medical worker can operate the relief pipe on-off valve to release the closed state after confirming the closed site.

Additionally, the pump may be a diaphragm type pump.

With this configuration, the pump unit can be miniaturized, and the dosing mechanism can be reduced in weight. Accordingly, a burden of the patient can be reduced when the patient is carrying the dosing mechanism.

Additionally, the present invention relates to a use method of a dosing mechanism, in which each of the above-mentioned dosing mechanisms is used, and when the discharge-side pipe is closed, the pump is suspended to keep a state in which the medicine cannot flow toward the patient in the discharge-side pipe, while the relief pipe on-off valve is opened.

With this configuration, an excessive amount of the medicinal solution can be eliminated from the medicine channel while the patient is suppressed from being dosed with the medicinal solution in a rush.

Additionally, the present invention relates to a pump unit for a dosing mechanism, including: a diaphragm type pump; pipes that are provided on a suction side and a discharge side of the pump; a relief pipe whose one end is connected to the pipe on the discharge side while the other end is located in a part whose pressure is lower than pressure inside the pipe on the discharge side when the medicine is dosed; and a relief pipe on-off valve that opens and closes the relief pipe.

With this configuration, in the dosing mechanism in which the aforementioned pump unit has been installed, the relief pipe on-off valve is opened before release of the closed state, so that an excessive amount of the medicinal solution staying in a section between the pump and the closed site can be eliminated from the medicine channel. Thus, the staying medicinal solution can be suppressed from flowing toward the patient due to the release of the closed state.

Additionally, the other end of the relief pipe may be connected to the pipe on the suction side.

With this configuration, in the dosing mechanism in which the aforementioned pump unit has been installed, the excessive amount of the medicinal solution staying in the section between the pump and the closed site can be returned to the suction-side pipe. Thus, the excessive medicinal solution can be used effectively.

Advantage of the Invention

According to the present invention, the staying medicinal solution can be suppressed from flowing toward the patient due to the release of the closed state. Thus, it is possible to suppress a patient from being dosed with a medicinal solution in a rush as soon as closed state is released even when the closing occurs in a pipe such as a tube.

BRIEF DESCRIPTION OF THE DRAWINGS

FIGS. 2(a)-2(d) show a body and a disposable portion according to the present embodiment, in which a cover portion has been removed. FIG. 2(a) is a front view, FIG. 2(b) is a right side view, FIG. 2(c) is a longitudinal sectional view with respect to the arrow direction A-A, and FIG. 2(d) is a back view.

FIGS. 3(a)-3(d) are schematic views showing the disposable portion (pump unit) according to the present embodiment. FIG. 3(a) is a front view, FIG. 3(b) is a view showing an internal structure of the disposable portion in front view, FIG. 3(c) is a right side view, and FIG. 3(d) is a back view.

FIG. 4(a) is a schematic view showing a flow of the medicinal solution during dosing in the disposable portion according to the present embodiment, and FIG. 4(b) is a schematic view showing a flow of the medicinal solution when the closed state is released.

FIG. 6(a) is a front view, FIG. 6(b) is a plan view, and FIG. 6(c) is a longitudinal sectional view.

MODE FOR CARRYING OUT THE INVENTION

Figure 1:
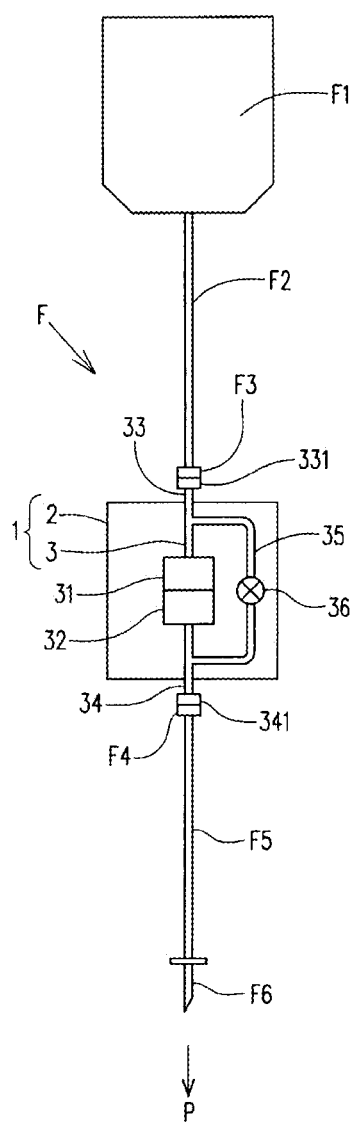
FIG. 1 is a schematic view showing a dosing route according to an embodiment of the present invention.

Next, the present invention will be described using an embodiment thereof. A dosing mechanism 1 according to the present embodiment includes a body 2, and a disposable portion (a pump unit or a dosing mechanism pump unit) 3 that is removably attached to the body 2. The dosing mechanism 1 is attached to the middle of a dosing route F from a medicine vessel F1 such as an infusion bag to a patient P, as shown in FIG. 1.

As shown in FIGS. 2(a) to 2(d), the body 2 is a part that holds the disposable portion 3 and performs various detections, controls and managements. A medicine-vessel-side tube F2 and a patient-side tube F5 are connected to the disposable portion 3 held by the body 2, as shown in FIG. 1. Although not shown for convenience of explanation, an openable/closeable cover portion is provided on the front side of the body 2. The cover portion abuts against side surfaces of a suction-side tube 33 and a discharge-side tube 34 of the disposable portion 3 when the cover portion is closed. The suction-side tube 33 and the discharge-side tube 34 will be described later. Incidentally, the upper side illustrated in FIGS. 2(a) to 2(d) corresponds to the medicine vessel F1 side (suction side) when the dosing mechanism 1 is in use, and the lower side likewise corresponds to the patient P side (discharge side) when the dosing mechanism 1 is in use.

The body 2 has a disposable portion mounting recess portion 22, which is a recess portion to which the disposable portion 3 can be fitted. A body-side electric contact (not shown) is provided in a bottom surface of the disposable portion mounting recess portion 22. When the disposable portion 3 is fitted to the disposable portion mounting recess portion 22, electric power for driving a pump 31 can be supplied from the body-side electric contact to the disposable portion 3. Above and below the disposable portion mounting recess portion 22 in FIGS. 2(a) to 2(d), tube mounting grooves 23 are formed. The suction-side tube 33 and the discharge-side tube 34 of the disposable portion 3 are disposed in the tube mounting grooves 23.

The body 2 is provided with sensors that can detect a solution feeding state of the disposable portion 3. As the sensors, pressure sensors 24 and a bubble sensor 25 are provided in the present embodiment. The pressure sensors 24 are provided at two places on the medicine vessel F1 side and the patient P side of the body 2. However, only one pressure sensor may be provided at a place on the medicine vessel F1 side or the patient P side.

The pressure sensors 24 are provided in positions corresponding to the suction-side tube 33 and the discharge-side tube 34 in the disposable portion 3 attached to the body 2. When pressure rises in each tube, the tube is inflated to expand the diameter of the tube. When the pressure falls in each tube, the tube shrinks to reduce the diameter of the tube. Using this phenomenon, the pressure sensors 24 detect pressure changes in the suction-side tube 33 and the discharge-side tube 34 respectively based on changes in diameters of the tubes 33 and 34.

Specifically, in each pressure sensor 24, as shown in FIGS. 2(a) to 2(c), a movable block 241 having a groove to which the tube 33 or 34 can be fitted is provided movably between the front side and the back side. An element 242 that can output a voltage proportional to a load applied thereto is disposed on the back side of the movable block 241 so as to abut against the movable block 241. The tubes 33 and 34 are regulated not to move to the front side by the cover portion (not shown) of the body 2. Therefore, when the movable block 241 moves in accordance with expansion/shrinkage of the tube 33 or 34, the voltage outputted from the element 242 changes in accordance with the load applied to the element 242. Thus, the pressure change in the tube 33 or 34 can be detected by the pressure sensor 24.

Assume that the dosing route F is closed in a middle section thereof due to bending or the like of a tube. In this case, when the dosing route F is closed on the upstream side from the pump 31 in the disposable portion 3, the pump 31 performs suction in spite of a state where a medicinal solution (liquid medicine filled in the medicine vessel F1) hardly flows from the medicine vessel F1 side. Due to the continuous driving of the pump 31, the internal pressure of the suction-side tube 33 becomes negative. Thus, the suction-side tube 33 shrinks. On the other hand, when the dosing route F is closed on the downstream side from the pump 31, the pump 31 performs discharge in spite of a state where the medicinal solution hardly flows to the patient P side. Due to the continuous driving of the pump 31, the internal pressure of the discharge-side tube 34 becomes positive. Thus, the discharge-side tube 34 is inflated. In this manner, occurrence of closing can be grasped by detection of the pressure sensors 24. Incidentally, in the disposable portion 3 according to the present embodiment, a bypass pipe 35 and a bypass on-off valve 36 are provided as a relief channel for relieving an excessive medicinal solution appearing at the time of the closing (see FIG. 3(b)). The relief channel will be described later.

In addition, the body 2 includes a control portion 261, an internal power supply portion 262, an external power supply input jack 263, a flow rate jack 264, and a communication jack 265. The control portion 261 performs pump control of the disposable portion 3, processing and storage of detection results of the sensors, etc. A battery is disposed in the internal power supply portion 262. A detection value of a flow rate sensor for detecting a dropping amount or the like is inputted to the flow rate jack 264. The flow rate sensor is attached to a not-shown drip cylinder located on the patient P side from the medicine vessel F1. The communication jack 265 serves to output dosing history data, sensor detection results, etc. In addition, though not shown, the body 2 also includes a speaker for outputting an alarm sound or the like, an LED lamp for indicating an alarm or the like, a sensor for detecting that the cover portion has been opened, and a liquid crystal display portion for displaying various pieces of information. In addition, the body 2 may include a part to which a band or the like for attaching the body 2 to a body of the patient P can be attached, or a part which can be attached to an infusion stand or the like for use in a medical institution.

As shown in FIGS. 3(a) to 3(d), the disposable portion 3 includes the pump 31, a free flow preventing valve 32, the suction-side tube (suction-side pipe) 33, the discharge-side tube (discharge-side pipe) 34, the bypass pipe (relief pipe) 35, and the bypass on-off valve (relief pipe on-off valve) 36. The pump 31, the free flow preventing valve 32, the bypass pipe 35 and the bypass on-off valve 36 are received integrally in a casing 37. Therefore, the disposable portion 3 can be attached to the body 2 and removed therefrom easily. The suction-side tube 33 and the discharge-side tube 34 are inserted to tube connection pipes 332 and 342 protruding from the casing 37. Connectors 331 and 341 which can be connected to the tubes F2 and F5 extending from the medicine vessel F1 and the patient P are provided at front ends of the suction-side tube 33 and the discharge-side tube 34. The tube connection pipes 332 and 342 protrude eccentrically to the front side from a flat surface and a bottom surface of the casing as shown in FIG. 3(c). Therefore, if the front side and the back side of the casing 37 are confused with each other when the disposable portion 3 is attached to the body 2, the tube connection pipes 332 and 342 are caught in the tube mounting grooves 23 of the body 2 so that the disposable portion 3 cannot be attached. It is therefore possible to prevent the disposable portion 3 from being erroneously attached to the body 2.

Incidentally, according to another embodiment, the outer shape of the part of the body 2 to which the disposable portion 3 can be attached may be formed into an asymmetrical shape, or concave portions or convex portions may be formed in asymmetric positions. In this manner, it is possible to prevent the disposable portion 3 from being erroneously attached to the body 2. Further, marking display (arrow display) may be provided in the disposable portion 3 so that erroneous attachment of the disposable portion 3 to the body 2 can be suppressed.

A disposable-portion-side electric contact 38 which can be connected to a body-side electric contact (not shown) is formed in the back surface of the casing 37. Accordingly, when the back surface of the casing 37 is aligned with the bottom surface of the disposable portion mounting recess portion 22 of the body 2 to establish electric connection between the body-side electric contact and the disposable-portion-side electric contact 38, electric conduction to the pump 31 can be established to drive the pump 31.

The pump 31 can suck medicine from the medicine vessel F1 and discharge the medicine to the patient P. As for the type of the pump, for example, a piston pump, a roller pump and a diaphragm type pump can be used. However, the diaphragm type pump is preferred because it does not require a motor. In the present embodiment, therefore, the diaphragm type pump is used. When the diaphragm type pump is used as the pump 31, the pump can be miniaturized because it does not require a motor. Thus, the disposable portion 3 can be also miniaturized, and the weight of the dosing mechanism 1 can be reduced. Accordingly, a burden of the patient P can be reduced when the patient P is carrying the dosing mechanism 1. Particularly there is a large merit for the patient P who has to be always dosed with medicine. In addition, the discharge amount of the medicinal solution can be controlled with high accuracy by the diaphragm type pump.

Figure 6A:
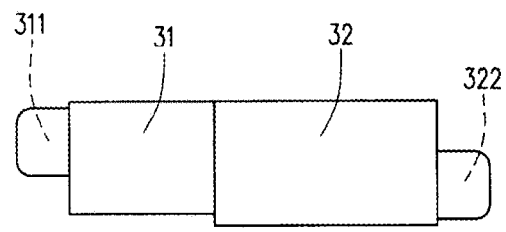
FIGS. 6(a)-6(c) are schematic views showing a pump and an anti-flow valve in the disposable portion according to the present embodiment.
Figure 6B:
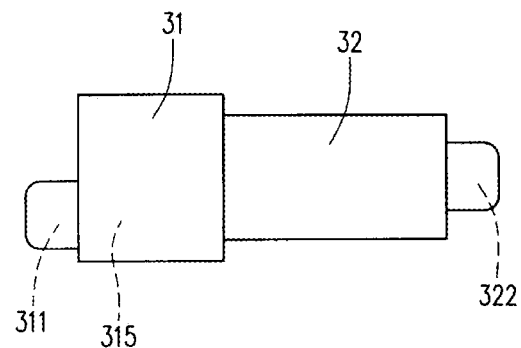
Figure 6C:
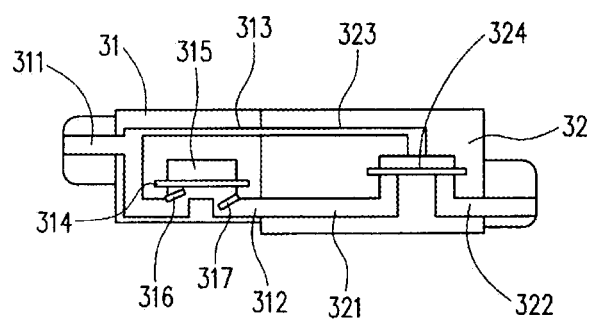

A pump using MEMS technology relating to an integrated device is used as the pump 31 according to the present embodiment. For example, a micro-pump disclosed in JP-A-2013-117211 is used. In the pump 31, as shown in FIG. 6(c), a diaphragm 314 made of a stainless steel thin plate is vibrated by a piezoelectric element so that the volume of a pump chamber 315 serving as a part for feeding the solution can repeat expansion and shrinkage. A valve 316 allowing the medicinal solution to flow only in the suction direction is provided on the suction side in the pump chamber 315, and a valve 317 allowing the medicinal solution to flow only in the discharge direction is provided on the discharge side. Due to the valves, the solution is fed from a suction-side channel 311 to a discharge-side channel 312.

Incidentally, a required volume of the pump 31 differs depending on an amount of the medicinal solution to be dosed. Therefore, a mark for specifying the volume may be indicated in the casing 37, or the shape of the casing 37 may be changed.

In addition, control contents of the pump 31 in the body 2 (control portion 261) differ depending on the volume of the pump 31. Therefore, when the mark indicated in the casing 37 or the shape of the casing 37 is changed in accordance with the volume of the pump 31 as described above, the body 2 may be configured to recognize the mark or the casing shape and to automatically change the control contents in accordance with the recognition. Further, an identifier such as an IC chip may be provided in the casing 37, and a unit for reading the identifier may be provided in the body 2. With this configuration, the control contents can be automatically changed only when the disposable portion 3 is attached to the body 2. Incidentally, when the identifier is provided as described above, a use history of the disposable portion 3 may be recorded in the identifier so that the disposable portion 3 removed after use cannot be used again.

The free flow preventing valve 32 is provided for preventing occurrence of an unintended flow passing through the pump 31 due to pressure of the medicinal solution caused by gravitation when the pump 31 is not being driven. As shown in FIG. 6(c), the free flow preventing valve 32 according to the present embodiment is connected to the discharge-side channel 312 and a balance channel 313 of the pump 31 so that the free flow preventing valve 32 can be integrated with the pump 31. Incidentally, as shown in FIG. 6(b), the width of the free flow preventing valve 32 is formed to be smaller than the width of the pump 31. Thus, there is a step between the both. As shown in FIG. 6(a), there is a positional deviation between a protruding part of the pump 31 where the suction-side channel 311 passes and a protruding part of the free flow preventing valve 32 where an exit-side main channel 322 passes. Due to the aforementioned step and the aforementioned positional deviation between the two protruding parts, the pump 31 and the free flow preventing valves 32 can be suppressed from being attached to the casing 37 on the wrong way around. Thus, the disposable portion 3 can be assembled efficiently.

In the free flow preventing valve 32, as shown in FIG. 6(c), an entrance-side main channel 321 (which is connected to the discharge-side channel 312 of the pump 31) and the exit-side main channel 322 are provided on one surface side of a diaphragm 324, and a balance channel 323 (which is connected to the balance channel 313 of the pump 31) is formed on the other surface side. In this configuration, a flow between the entrance-side main channel 321 and the exit-side main channel 322 occurs only when the diaphragm 324 moves. That is, when only the pressure of the medicinal solution from the medicine vessel F1 is applied onto the diaphragm 324, the pressure in the entrance-side main channel 321 and the pressure in the balance channel 323 are balanced. Thus, the diaphragm 324 stands still not to generate any flow in the free flow preventing valve 32. On the other hand, when the pump 31 is being driven, the pressure of the medicinal solution pushed out by the pump 31 is larger than the internal pressure of the balance channel 323. Thus, a flow from the entrance-side main channel 321 to the exit-side main channel 322 is generated. Due to the free flow preventing valve 32 thus provided, a flow of the medicinal solution can be generated in the disposable portion 3 only when the pump 31 is being driven. It is therefore possible to prevent the patient P from being unintentionally dosed with the medicinal solution.

The suction-side tube 33 is a tube extending from the pump 31 toward the medicine vessel F1. The discharge-side tube 34 is a tube extending from the pump 31 toward the patient P. The tubes 33 and 34 are formed of soft resin such as silicone rubber. As will be described later, changes in diameters of the tubes 33 and 34 are detected by the pressure sensors 24. Therefore, regarding the tubes 33 and 34, at least the parts to be disposed in the pressure sensors 24 have to be formed within predetermined error ranges as to their materials (such as resin compositions, densities, etc.), tube thicknesses, and tube diameters. Incidentally, according to another embodiment, in which changes in pressure are not detected using any piping, not soft tubes but hard pipes may be used in the disposable portion 3.

The connectors 331 and 341 are provided at the front ends of the tubes 33 and 34 respectively. The connectors 331 and 341 are general-purpose articles made of hard resin. As shown in FIG. 1, the connectors 331 and 341 are connected to the medicine-vessel-side tube F2 and the patient-side tube F5 (respectively including connectors F3 and F4 whose shapes have male-female relations to the connectors 331 and 341 of the disposable portion 3 so that the connectors F3 and F4 can be connected to the connectors 331 and 341), for example, by screwing. Due to the connectors 331 and 341, the disposable portion 3 and the medicine-vessel-side tube F2 can be separated from each other, and the disposable portion 3 and the patient-side tube F5 can be separated from each other. Thus, distances of the medicine vessel F1 and the patient P from the dosing mechanism 1 can be set desirably. Accordingly, the tubes F2 and F5 are hardly impeditive when the patient P is carrying the dosing mechanism 1.

Incidentally, the connector 331 or 341 may be disposed at a front end of at least one of the suction-side tube 33 and the discharge-side tube 34. When a connector is provided on only one side, the disposable portion 3 includes up to the medicine vessel F1 (or a not-shown drip cylinder, which is disposed on the patient P side from the medicine vessel F1) on the side where no connector is provided. On the opposite side with respect to the dosing mechanism 1, the disposable portion 3 includes up to a needle F6 to be inserted into the patient P.

The bypass pipe 35 connects the suction-side tube 33 and the discharge-side tube 34 to each other without interposing the pump 31 therebetween. As shown in FIG. 3(b), the bypass pipe 35 branches from a suction-side pipe 333 and a discharge-side pipe 343 inside the casing 37 (in the present embodiment, the bypass pipe 35 branches from the bypass on-off valve 36 located in an end portion of the discharge-side pipe 343).

Figure 4A:
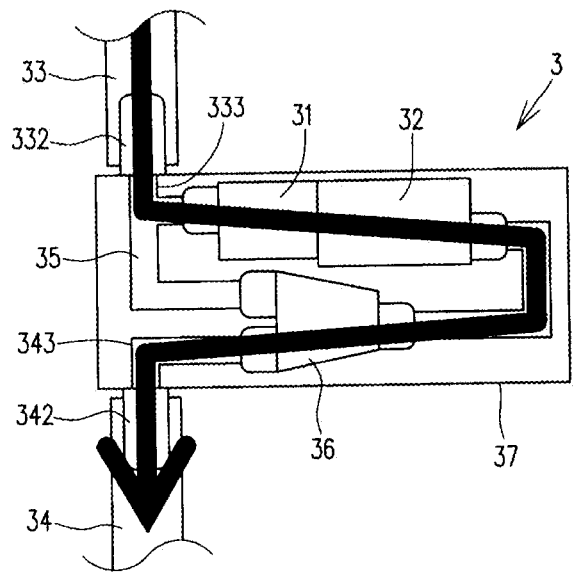
FIGS. 4(a)-4(b) are schematic views showing a flow of a medicinal solution.

At the time of dosing, as shown by the arrow in FIG. 4(a), the medicinal solution entering the casing 37 from the tube connection pipe 332 passes through the suction-side pipe 333 in the casing 37, the pump 31, the free flow preventing valve 32, the bypass on-off valve 36, and the discharge-side pipe 343 in the casing 37, sequentially. The medicinal solution is then discharged from the tube connection pipe 342 in the casing 37. Incidentally, in the bypass on-off valve 36, a channel through which the medicinal solution can pass without stopping is formed in parallel with a channel which can be opened and closed by the bypass on-off valve 36. At a normal operation (except when the bypass on-off valve 36 is operated to be open), the medicinal solution passes through the channel through which the medicinal solution can pass without stopping.

Figure 4B:
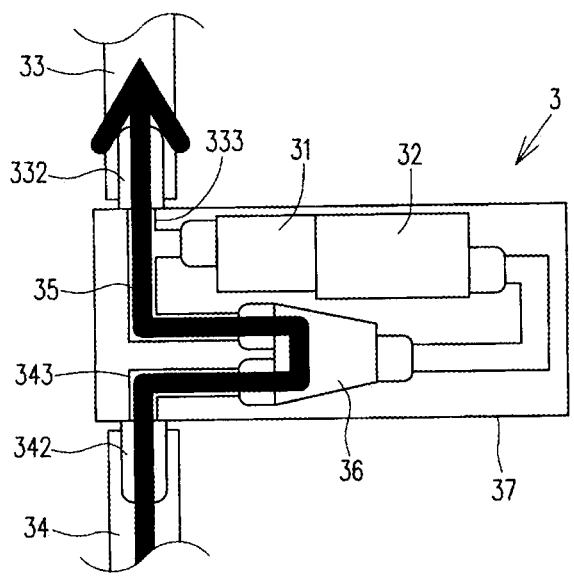

On the other hand, when the dosing route F is closed and the bypass on-off valve 36 is opened, as shown by the arrow in FIG. 4(b), of the medicinal solution staying in the discharge-side tube 34, an excessive amount passes through the tube connection pipe 342 in the casing 37, the discharge-side pipe 343 in the casing 37, the bypass on-off valve 36 (of the bypass on-off valve 36, the channel which can be opened and closed), the bypass pipe 35, and the suction-side pipe 333 in the casing 37, sequentially. Then the medicinal solution is discharged from the tube connection pipe 332 in the casing 37.

Due to the existence of the bypass pipe 35 thus configured, when the bypass on-off valve 36 is open, the suction-side tube 33 and the discharge-side tube 34 are made to communicate with each other, so that an excessive amount of the medicinal solution can be returned to the suction-side tube 33 if the dosing route F is closed.

Figure 5:
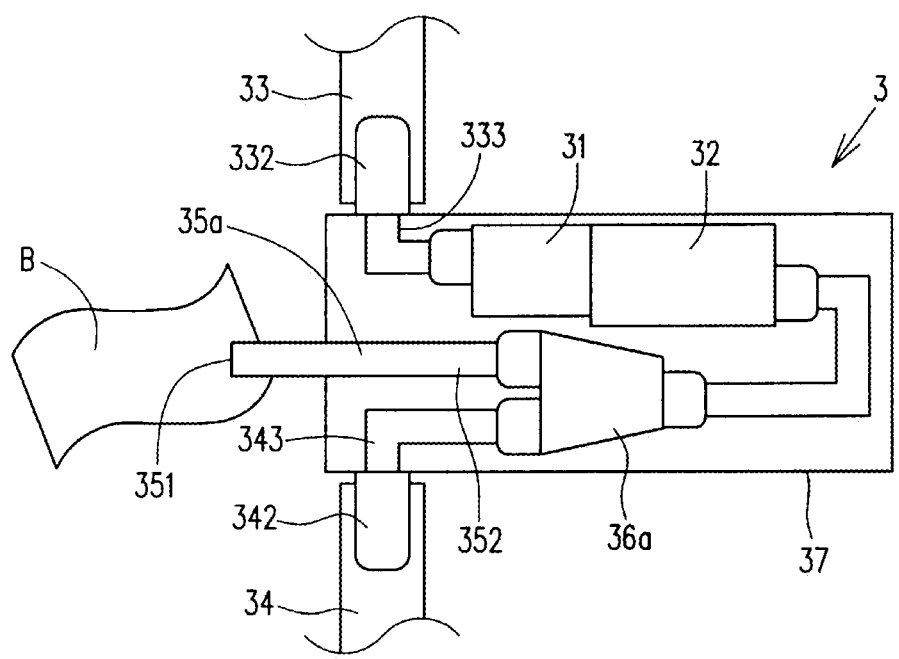
FIG. 5 is a schematic view showing an internal structure of a disposable portion according to another embodiment of the present invention.

In the present embodiment, as shown in FIG. 3(b), one end 351 of the relief pipe (the bypass pipe 35 in the present embodiment) is connected to the suction-side pipe 333, and the other end 352 is connected the discharge-side pipe 343 through the bypass on-off valve 36. However, the present invention is not limited to such a configuration. For example, the present invention may have a configuration as shown in FIG. 5. In a relief pipe 35a shown in FIG. 5, one end 351 is opened to air while the other end 352 is connected to the discharge-side pipe 343 through a relief pipe on-off valve 36a corresponding to the bypass on-off valve 36. The opened part is covered with a vessel B. In this manner, an end portion (the one end 351 in the example shown in FIG. 5) of the relief pipe 35a can be disposed in a part whose pressure is lower than the pressure inside the discharge-side pipe when medicine is being dosed. In addition, in the example shown in FIG. 5, the vessel B is provided for recovering an excessive amount of the medicinal solution leaking from the one end 351 of the relief pipe 35a when the bypass on-off valve 36 is open. However, an absorber may be instead disposed for absorbing the leaking excessive amount of the medicinal solution. Incidentally, in the example of FIG. 5, it is necessary to provide a check valve or the like to prevent the air from entering the discharge-side pipe 343 from the one end 351 of the relief pipe 35a. In the example of FIG. 5, the relief pipe on-off valve 36a corresponding to the bypass on-off valve 36 is located at the other end 352 of the relief pipe 35a. However, the position of the relief pipe on-off valve 36a is not limited. For example, the relief pipe on-off valve 36a may be disposed at the one end 351 or between the two ends.

When a pump in which the volume of a solution feeding part (the pump chamber 315 shown in FIG. 6(c)) repeats expansion and shrinkage, such as a diaphragm type pump, is used as the pump 31, a backward flow passing through the pump 31 can be prevented due to the configuration of the pump 31 even if the tube 34 or F5 connected to the discharge side of the disposable portion 3 is closed. As a result, the pump 31 may be driven continuously until a large amount of the medicinal solution stays in a section between the pump 31 and the closed site. Of the medicinal solution staying in the section between the pump 31 and the closed site, an excessive amount is returned to the suction side from the pump 31. On this occasion, the excessive medicinal solution is passed through the bypass pipe 35 and the bypass on-off valve 36.

As shown in FIG. 3(b), the bypass on-off valve 36 is provided in an end portion of the bypass pipe 35 so that the bypass on-off valve 36 can open and close the channel of the bypass pipe 35. The bypass on-off valve 36 is configured to be opened manually. A medical worker or the patient P can push a button 361 shown in FIG. 3(a) to thereby open the bypass on-off valve 36. When the medical worker or the patient P releases his/her finger from the button 361, the bypass on-off valve 36 is automatically closed by a spring or the like. The reason why the bypass on-off valve 36 is not automatically closed is because the medical worker or the patient P should confirm the closed site and investigate a cause of the closing when the dosing route F is closed in its middle. Thus, proper countermeasures can be taken when the dosing route F has been closed. In some estimated situation, the bypass on-off valve 36 that can be automatically opened when the pressure of the bypass pipe 35 or the like is beyond a predetermined pressure may be used.

The disposable portion 3 according to the present embodiment is made disposable. Therefore, the dosing mechanism 1 can be used sanitarily and safely. Although depending on the kind of medicine or the use state, the disposable portion 3 is replaced typically when it is used for about three days, or in a longest case when it is used for about thirty days. When the disposable portion 3 is made disposable, it is not necessary to perform inspection of discharge accuracy, which should be performed by a medical engineer (ME) in a medical institution. Accordingly, the dosing mechanism 1 can be managed easily in the medical institution. In the future, the dosing mechanism 1 may be able to be managed by a nurse or the like in each ward without using power of any medical engineer.

In addition, if, of the suction-side tube 33 and the discharge-side tube 34, at least the parts corresponding to the pressure sensors 24 are managed as to their materials, dimensional errors, etc., each of the tubes located correspondingly to the pressure sensors 24 can be arranged substantially with the same diameter or the same hardness (ease of changing in diameter) even when the disposable portion 3 is replaced. Accordingly, the tube can be prevented from varying in diameter or hardness as in a case where each tube prepared by a medical institution is connected to the dosing mechanism. It is therefore possible to surely detect a change in pressure.

Next, a method for using the dosing mechanism 1 will be described briefly. First, the tube F2 extending from the medicine vessel F1 and the tube F5 extending from the patient P side (the needle F6 is attached to the tube F5 in advance when the tube 5 is not provided with the needle F6) are connected to the disposable portion 3. Then the disposable portion 3 to which the tube F2 and the tube F5 have been connected is connected to the body 2. On this occasion, the disposable portion 3 is in the state shown in FIG. 1. If necessary, a drip cylinder or a flow rate sensor may be attached. Next, bubbles are purged from the dosing route F. The needle F6 is then inserted into the patient P. Next, driving the pump 31 is started. As a result, the medicinal solution is sent into the body of the patient P by the pump 31.

When the dosing route F is closed (particularly closed in a section of the dosing route F on the patient P side from the pump 31), the pressure sensors 24 detect the closing, and the control portion 261 issues notification of an alarm (notification using an alarm sound or lighting an alarm lamp). In response thereto, a medical worker or the patient P suspends the pump 31 (the pump 31 may be automatically suspended interlocking with the notification of the alarm). In addition, the medical worker or the patient P closes an on-off valve (not shown) in a case where the on-off valve is provided on the patient P side from the body 2. Then, the medical worker or the patient P opens the bypass on-off valve 36 of the disposable portion 3. After that, the medical worker or the patient P confirms the closed site and releases the closed state (for example, extends a tube which has been bent, in order to secure a flow channel). In this manner, the bypass on-off valve 36 is opened before release of the closed state, so that an excessive amount of the medicinal solution staying in a section between the pump 31 and the closed site can be returned to a section of the dosing route F on the medicine vessel F1 side from the pump 31. In safety, the staying medicinal solution can be suppressed from flowing toward the patient P due to the release of the closed state. In addition, the medicinal solution returned to the section on the medicine vessel F1 side is dosed to the patient P again by the pump 31. Thus, the excessive medicinal solution caused by the occurrence of the closing can be used effectively. After the release of the closed state, the on-off valve is opened in a case where the on-off valve is provided on the patient P side. Thus, driving of the pump 31 is resumed to resume dosing the medicinal solution.

The present application is based on Japanese Patent Application No. 2014-240045 filed on Nov. 27, 2014, the contents of which are incorporated herein by reference.

The embodiment of the present invention has been described above. However, the present invention is not limited to the embodiment. Various changes may be made on the present invention without departing from the gist of the invention.

DESCRIPTION OF REFERENCE NUMERALS AND SIGNS 1 dosing mechanism
2 body
24 pressure sensor
3 disposable portion, pump unit (dosing mechanism pump unit)
31 pump
315 solution feeding part, pump chamber
33 suction-side pipe, suction-side tube
331 connector (suction side)
34 discharge-side pipe, discharge-side tube
341 connector (discharge side)
35 relief pipe, bypass pipe
351 one end of relief pipe (bypass pipe)

352 the other end of relief pipe (bypass pipe)
36 bypass on-off valve (relief pipe on-off valve)
F1 medicine vessel
P patient

The invention claimed is:

1. A dosing mechanism for dosing a patient with liquid medicine filled in a medicine vessel, comprising: a body; and a pump unit that is attached to the body,
wherein the pump unit comprises:
a pump in which a volume of a solution feeding part therein repeats expansion and shrinkage, thereby sucking the medicine from the medicine vessel and discharging the medicine to the patient;
a suction-side pipe that extends from the pump toward the medicine vessel;
a discharge-side pipe that extends from the pump toward the patient;
a relief pipe whose one end is connected to the discharge-side pipe while the other end is located in a part whose pressure is lower than pressure inside the discharge-side pipe when the medicine is dosed; and
a relief pipe on-off valve that opens and closes the relief pipe,
wherein an excessive amount of the medicine staying in the discharge-side pipe passes through the relief pipe when a dosing route is closed and the relief pipe on-off valve is opened.

2. The dosing mechanism according to claim 1, wherein the other end of the relief pipe is connected to the suction-side pipe.

3. The dosing mechanism according to claim 1, wherein the relief pipe on-off valve is configured to be opened manually.

4. The dosing mechanism according to claim 1, wherein the pump is a diaphragm type pump.

5. A use method of a dosing mechanism,
wherein the dosing mechanism according to claim 1 is used, and
when the discharge-side pipe is closed, the pump is suspended to keep a state in which the medicine cannot flow toward the patient in the discharge-side pipe, while the relief pipe on-off valve is opened.

6. The dosing mechanism according to claim 1, wherein the other end of the relief pipe is opened to air.

7. A pump unit for a dosing mechanism, comprising:
a diaphragm type pump;
pipes that are provided on a suction side and a discharge side of the pump;
a relief pipe whose one end is connected to the pipe on the discharge side while the other end is located in a part whose pressure is lower than pressure inside the pipe on the discharge side when the medicine is dosed; and
a relief pipe on-off valve that opens and closes the relief pipe,
wherein an excessive amount of the medicine staying in the discharge-side pipe passes through the relief pipe when a dosing route is closed and the relief pipe on-off valve is opened.

8. The pump unit for a dosing mechanism according to claim 7, wherein the other end of the relief pipe is connected to the pipe on the suction side.

9. The pump unit for a dosing mechanism according to claim 7, wherein the other end of the relief pipe is opened to air.

* * * * *